United States Patent [19]
Hotier et al.

[11] Patent Number: 5,948,950
[45] Date of Patent: Sep. 7, 1999

[54] PROCESS FOR SEPARATING PARA-XYLENE, COMPRISING AN ADSORPTION STEP WITH INJECTION OF WATER AND A CRYSTALLIZATION STEP

[75] Inventors: Gérard Hotier; Alain Methivier, both of Rueil-Malmaison; Annick Pucci, Croissy-sur-Seine, all of France

[73] Assignee: Institut Francais du Petrole, Rueik-Malmaison, France

[21] Appl. No.: 08/992,968

[22] Filed: Dec. 18, 1997

[30] Foreign Application Priority Data

Dec. 20, 1996 [FR] France ..................... 96 15930

[51] Int. Cl.⁶ ..................... C07C 7/13; C07C 7/00
[52] U.S. Cl. ............... 585/828; 585/805; 585/826; 585/827; 208/310 Z
[58] Field of Search ................... 585/828, 826, 585/827, 805, 812; 208/310 Z

[56] References Cited

U.S. PATENT DOCUMENTS

| | | | |
|---|---|---|---|
| 3,420,772 | 1/1969 | Eck et al. | 208/310 Z |
| 3,422,004 | 1/1969 | Padrta | 208/310 Z |
| 3,531,400 | 9/1970 | Wehner et al. | 208/310 Z |
| 3,732,326 | 5/1973 | Chen | 585/820 |
| 3,734,974 | 5/1973 | Neuzil | 260/674 SA |
| 3,895,080 | 7/1975 | Davis | 585/831 |
| 4,705,909 | 11/1987 | Yan | 585/828 |
| 5,177,295 | 1/1993 | Oroskar et al. | 585/805 |
| 5,284,992 | 2/1994 | Hotier et al. | 585/805 |
| 5,401,476 | 3/1995 | Hotier et al. | 422/222 |
| 5,629,467 | 5/1997 | Hotier et al. | 585/805 |

FOREIGN PATENT DOCUMENTS

| | | |
|---|---|---|
| 2089639 | 1/1972 | France . |
| 96/20908 | 7/1996 | WIPO . |

*Primary Examiner*—Walter D. Griffin
*Attorney, Agent, or Firm*—Millen, White, Zelano & Branigan, P.C.

[57] ABSTRACT

A process for separating para-xylene from a $C_8$ feed in a simulated moving bed comprises a step for adsorption on a zeolite and desorption using a desorbent delivering an extract and a raffinate, and an extract crystallization step. A stream of water is introduced into the feed, into the desorbent and/or into the stream for recycling one flux in the column, such that the weighted average of the amounts of water measured in the extract and in the raffinate is in the range 1 to 200 ppm. The ratio S/F of the desorbent flow rate to that of the feed during the adsorption and desorption step is in the range 0.6 to 2.5.

26 Claims, 5 Drawing Sheets

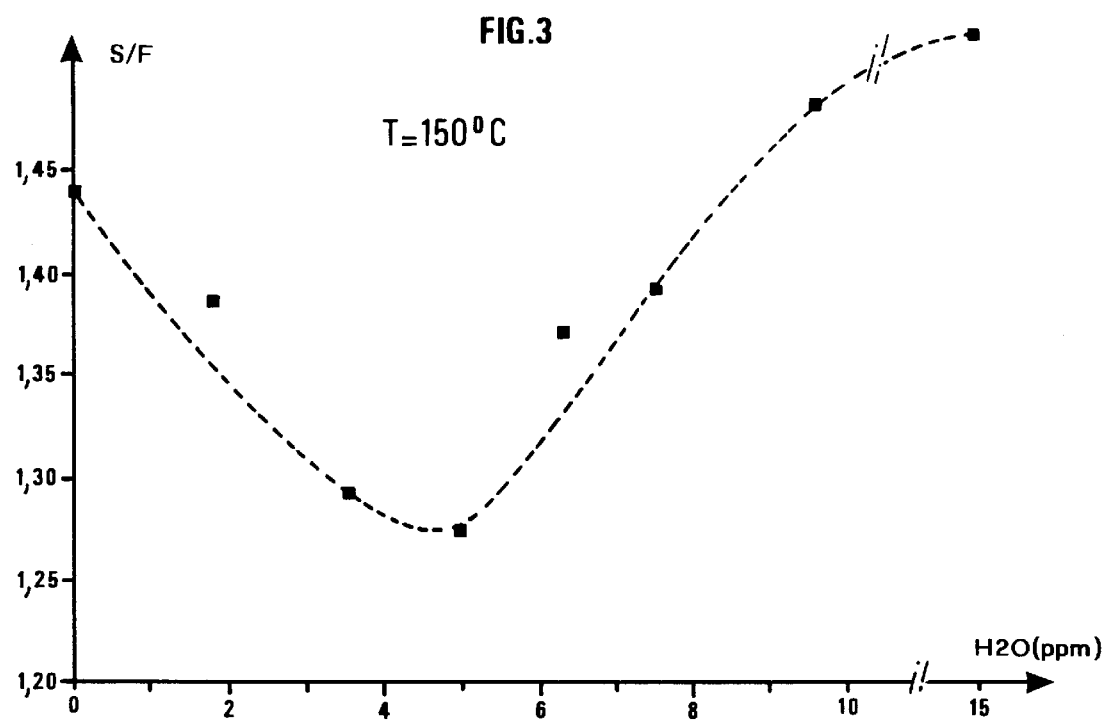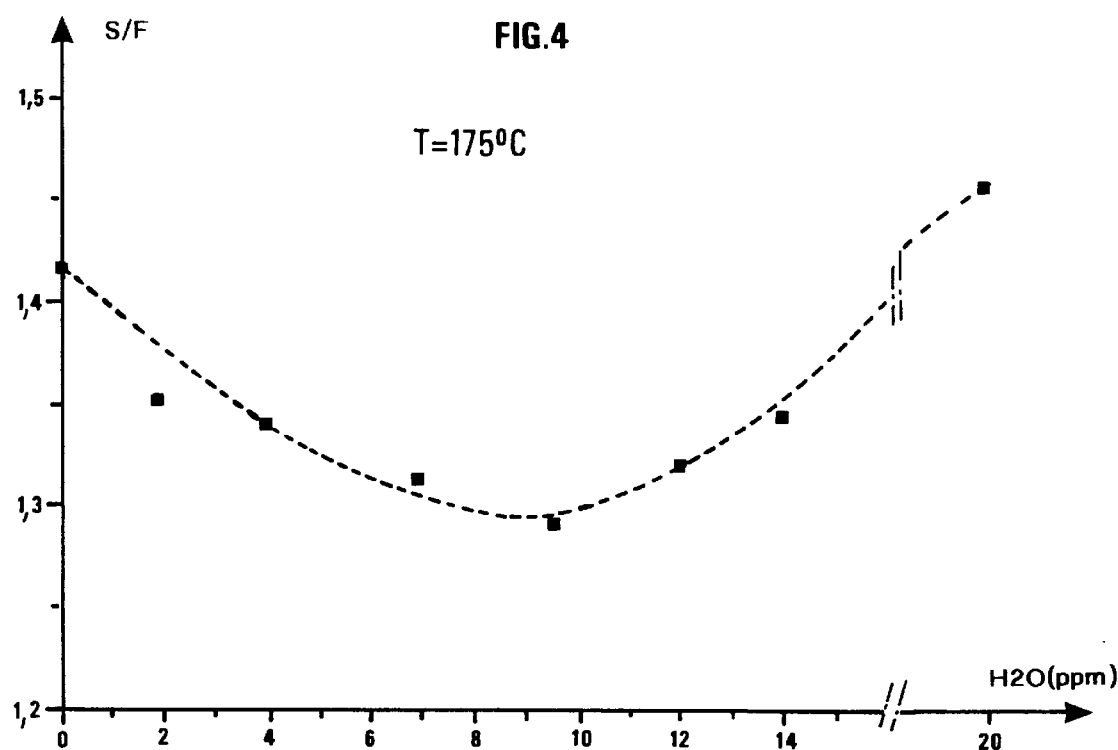

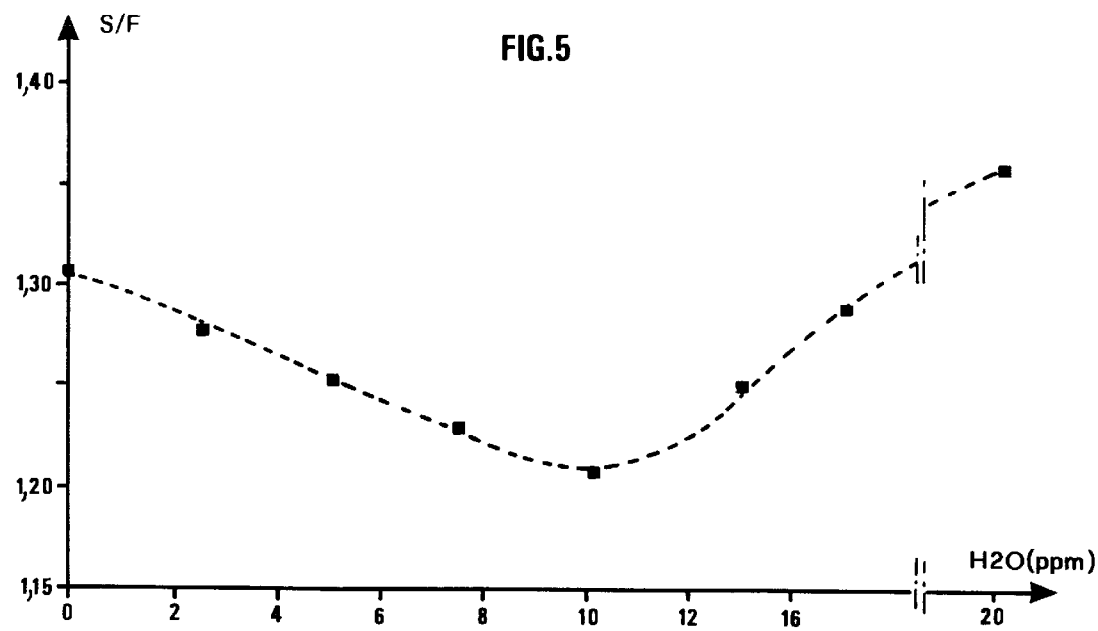
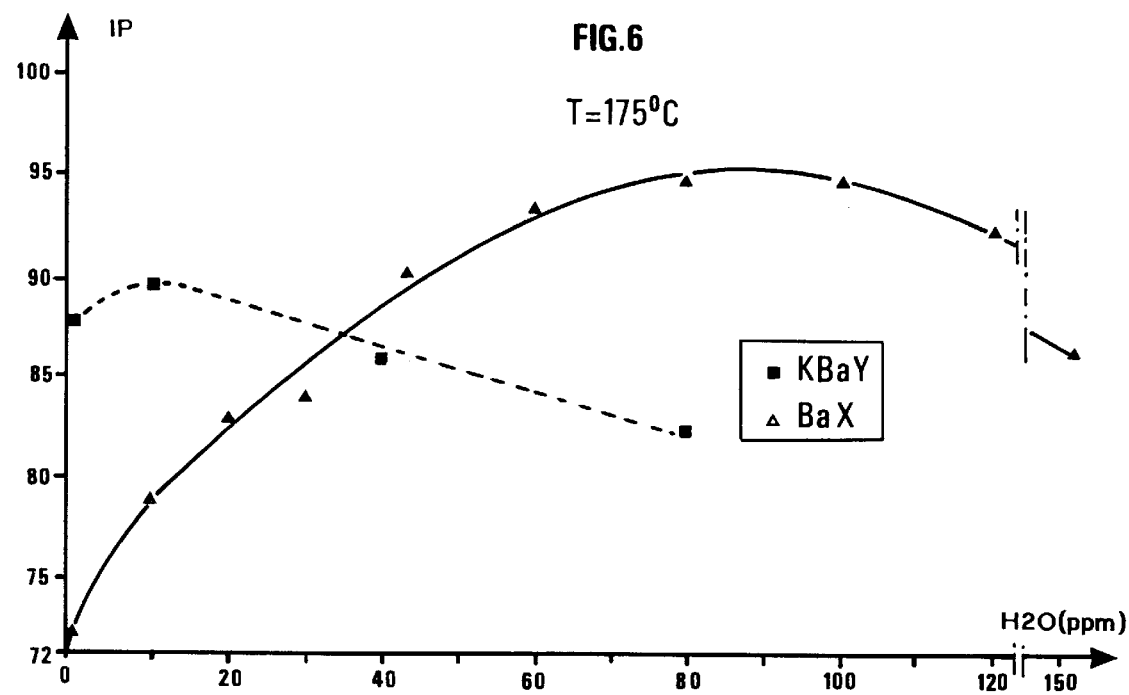

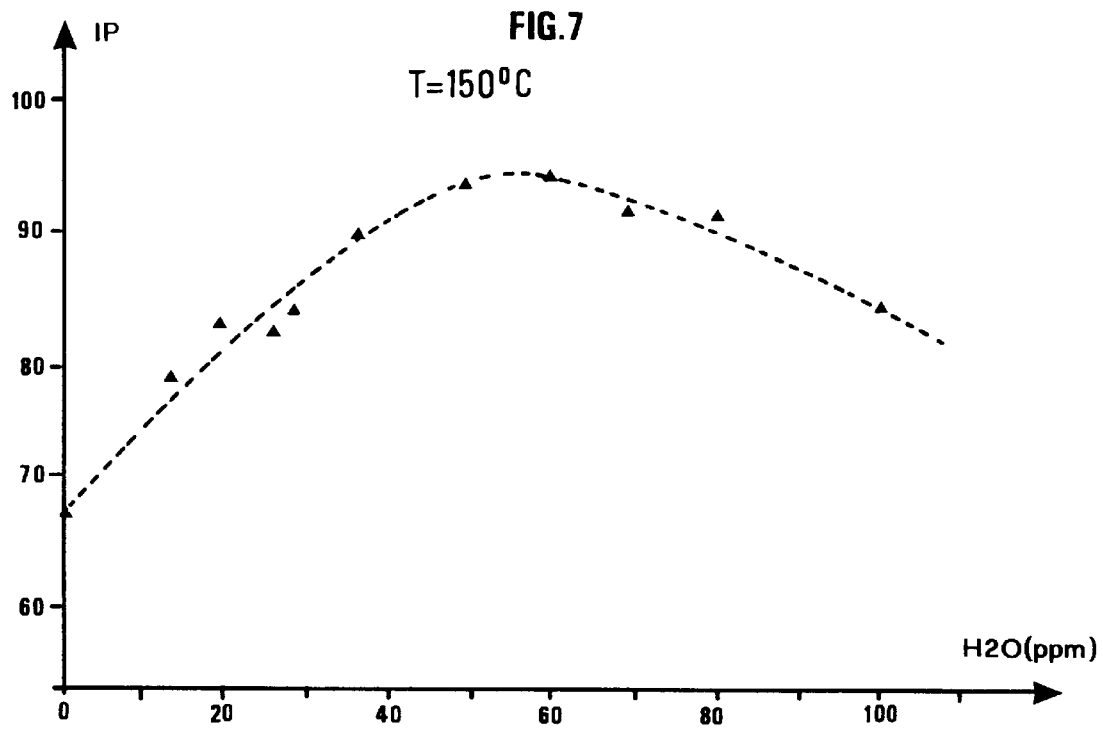
FIG.7 T=150°C
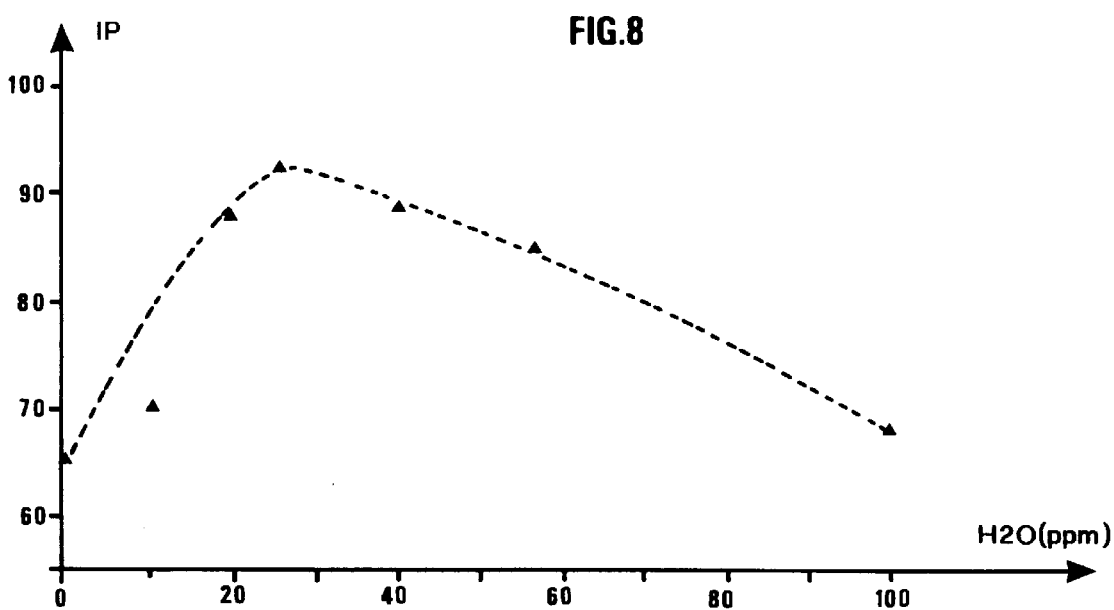
FIG.8

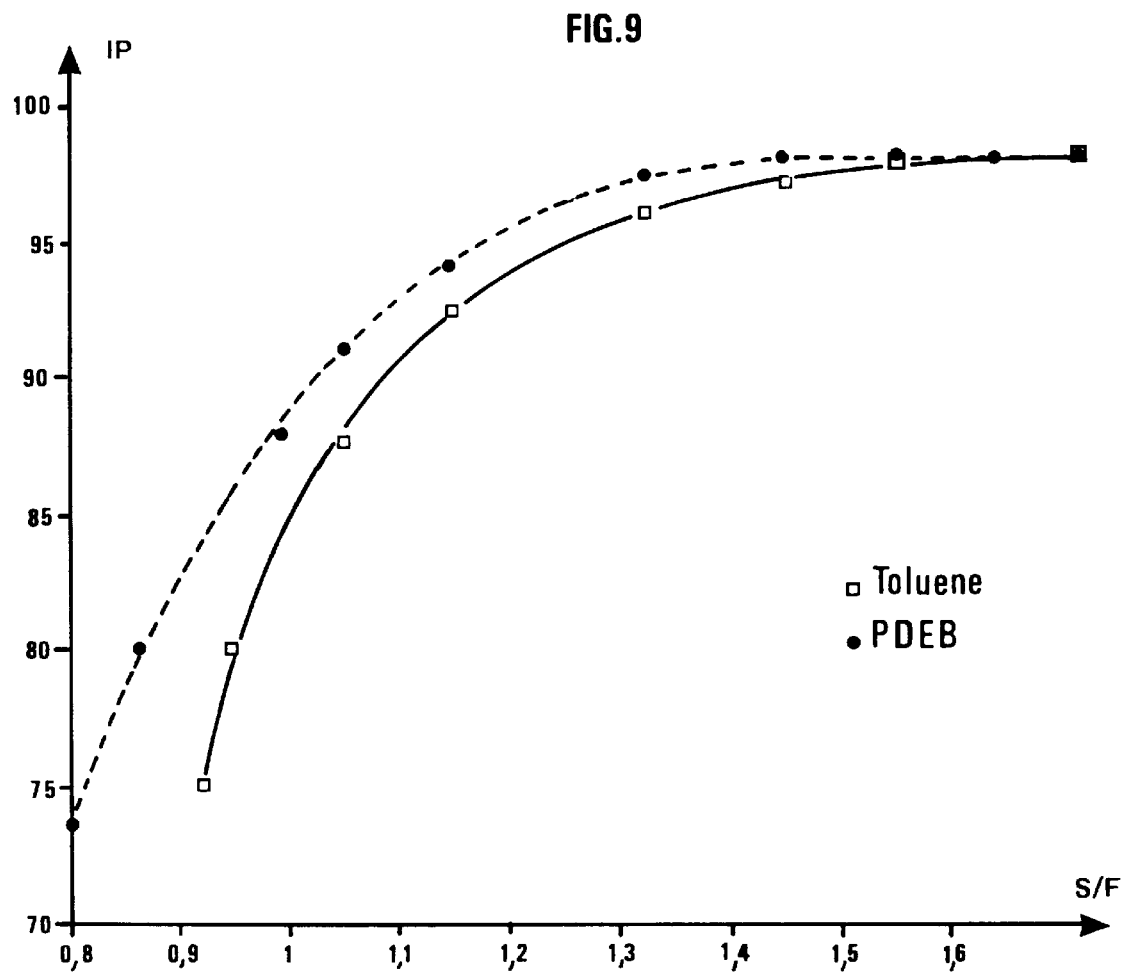

ns the use of KY zeolite
PROCESS FOR SEPARATING PARA-XYLENE, COMPRISING AN ADSORPTION STEP WITH INJECTION OF WATER AND A CRYSTALLIZATION STEP

FIELD OF THE INVENTION

The invention concerns a process for separating para-xylene from a mixture of $C_8$ aromatic isomers containing para-xylene, with improved productivity and reduced operating costs.

It is applicable to the preparation of very high purity para-xylene for the synthesis of terephthalic acid, an intermediate in the nylon manufacturing industry.

BACKGROUND OF THE INVENTION

The prior art is described in French patent application FR-A-2 089 639.

United States patent U.S. Pat. No. 5,401,476, which is hereby incorporated by reference, describes a combination of separation by simulated counter-current adsorption and crystallization to produce high purity para-xylene in a more economical manner than in a single step. The basic principles of that combination are as follows:

The simulated moving bed separation step is controlled in a different way to that for the direct production of high purity para-xylene. The feed flow rate is such that the flow rates in zone 2 and zone 3 (feed flow rate=flow rate in zone 2–flow rate in zone 3) cannot simultaneously produce an extract containing pure para-xylene and a raffinate which is free of para-xylene. The feed flow rate (and thus the productivity) is increased by reducing the flow rate in zone 2. It is thus impossible to obtain pure para-xylene (+than 98%). Further, the solvent flow rate is also reduced with respect to a "high purity" system in particular by increasing the flow rate in zone 4 above a threshold. The increase in productivity and the reduction in operating costs linked to the use of less solvent is to the detriment of purity.

In the crystallization step, a mixture containing 75% to 98% of para-xylene, more advantageously 85% to 95% of para-xylene, is treated to re-use pre-existing crystallisers in units based on crystallization schemes in two principal steps. A crystallization temperature which is preferably −15° C. to +15° C. is used so as not to consume frigories at a low heat level. In the most favourable cases, there is an additional synergy in using the same solvent as the desorbent in the adsorption step and as a rinsing solvent for the crystals in the crystallization step, which is different to the case for direct production of high purity para-xylene alone. However, when the feed adsorption step is carried out on the adsorbent with a high desorbent to feed ratio, for example over 1.3, very high purity of the desired product is obtained, in general over 95%. The higher the purity of the product, the more it can fluctuate. It is thus easy to imagine that when the purification step by crystallization, which can produce over 99% purity, is calculated for a feed of set purity which does not fluctuate, the operation of the crystalliser is disturbed.

U.S. Pat. No. 3,734,974 describes the use of X or Y zeolites exchanged with cations from group IA and/or group IIA (or a combination of the 2) with a controlled amount of water in the zeolite (1% to 5%) for the separation of para-xylene in a simulated moving bed (presumed to be high purity in the absence of any mention of low purity para-xylene). The desorbents used are, for example, toluene, or para-diethylbenzene or diethylbenzenes as a mixture or a mixture of these constituents with a paraffinic cut. Adding water, in particular to K BaX and BaX zeolites, brings about a very significant improvement of para-xylene-ethylbenzene and para-xylene-meta-xylene selectivities.

U.S. Pat. No. 4,778,946 describes the use of KY zeolite containing up to 10% of water and up to 4% of either methanol or ammonia for the separation of ethylbenzene and meta-xylene from feeds which are free of para-xylene so as not only to maximise the ethylbenzene-meta-xylene selectivity but also to obtain a desorbent-ethylbenzene selectivity as close as possible to 1. The desorbent/feed ratio used is 2/1. This document specifies that a desorbent which is too strongly adsorbed does not allow good separation and a desorbent which is too weakly adsorbed causes too excessive a demand for desorbent. It recornmends that the ethylbenzene-meta-xylene selectivity should be at least 3.0 and that the ethylbenzene-desorbent selectivity is in the range 1 to 2.

U.S. Pat. No. 5,401,476 does not suggest operating in the presence of water, as the hydrocarbons are anhydrous.

U.S. Pat. No. 3,734,974 does not suggest the possible importance of injecting water into a system where high purity para-xylene is not desired and does not recognise the role which water could play on the para-xylene-desorbent selectivity.

U.S. Pat. No. 4,778,946 teaches that water can modify the ethylbenzene-desorbent selectivity only in the case of feeds which are free of para-xylene. Neither U.S. Pat. No. 3,734,974 nor U.S. Pat. No. 4,778,946 suggests a simple and practical means not of controlling the water content in the zeolite but rather of aiming to control the water content in the hydrocarbons in contact with the zeolite.

SUMMARY OF THE INVENTION

The invention aims to overcome the disadvantages of the prior art. More precisely, the first aim of the invention is to carry out a process for separating high purity para-xylene by combining a simulated moving bed adsorption step and a crystallization step, where the simulated moving bed adsorption step includes operating at a reduced ratio of solvent to feed due to continuous injection of water into the streams which supply the adsorption column(s).

The second aim of the invention is to favourably change the para-xylene-desorbent selectivity so as to obtain an optimum value which can reduce the desorbent demand. The skilled person would be surprised that injecting water does not increase the purity at constant yield and productivity nor increase the yield at a fixed purity and productivity, nor increase the productivity at constant yield and purity, but reduces the desorbent demand at constant purity and productivity.

A third aim of the invention is to optimise the amount of water in the hydrocarbon effluents as a function of the nature of the adsorbing zeolite and the compensating cations and as a function of temperature.

Introducing a suitable quantity of water into the adsorption columns by means of the streams entering it, combined with a limited quantity of desorbent with respect to the quantity of feed produces very good results.

More precisely, the invention concerns a process for separating para-xylene from a feed comprising a mixture of aromatic $C_8$ isomers containing para-xylene, comprising a step for adsorption and desorption of isomers in the mixture in at least one column containing a zeolite, the adsorption and desorption step delivering, under suitable conditions, at least one desorbent, a fraction which is rich in para-xylene and a fraction which is depleted in para-xylene, the process further comprising at least one step for crystallizing the fraction which is rich in para-xylene which delivers pure para-xylene, the process being characterized in that a stream of water is introduced into the feed and/or the desorbent and/or into a recycling stream for one flux in the column, such that the weighted average of the water contents measured in the fraction which is rich in para-xylene and in the fraction which is depleted in para-xylene is in the range 1 to 250 ppm, advantageously in the range 3 to 120 ppm (parts per million), and in that the ratio S/F of the flow rate of the desorbent to that of the feed during the adsorption and desorption step is in the range 0.6 to 2.5, advantageously in the range 0.8 to 1.5, and preferably in the range 1 to 1.35.

We have determined the optimum results resulting from the above combination as a function of the nature of the zeolite, its compensating cations and the operating temperature.

Thus in a first implementation of the process, the adsorption and desorption step is carried out at a temperature of 140° C. to 160° C. with a Y zeolite exchanged with barium and potassium, the weighted average of the water contents is in the range 3 to 6 ppm and the S/F ratio is in the range 1.15 to 1.35.

In a second implementation of the process, the adsorption and desorption step is carried out at a temperature of 165° C. to 185° C. with a Y zeolite exchanged with barium and potassium, the weighted average of the water contents is in the range 6 to 12 ppm and the S/F ratio is in the range 1.10 to 1.35.

In a third implementation of the process, the adsorption and desorption step is carried out at a temperature of 140° C. to 160° C. with an X zeolite exchanged with barium, the weighted average of the water contents is in the range 45 to 70 ppm and the S/F ratio is in the range 1 to 1.25.

In a fourth implementation of the process, the adsorption and desorption step is carried out at a temperature of 165° C. to 185° C. with an X zeolite exchanged with barium, the weighted average of the water contents is in the range 60 to 130 ppm, preferably in the range 90 to 110 ppm, and the S/F ratio is in the range 0.95 to 1.2.

In a fifth implementation of the process, the adsorption and desorption step is carried out at a temperature of 140° C. to 160° C. with a Y or X zeolite exchanged with potassium, the weighted average of the water contents is in the range 5 to 10 ppm and the S/F ratio is in the range 1.2 to 1.4.

In a sixth implementation of the process, the adsorption and desorption step is carried out at a temperature of 165° C. to 185° C. with an X zeolite exchanged with potassium, the weighted average of the water contents is in the range 10 to 20 ppm and the S/F ratio is in the range 1.2 to 1.4.

In a seventh implementation of the process, the adsorption and desorption step is carried out at a temperature of 110° C. to 130° C. with an X zeolite exchanged with barium, the weighted average of the water contents is in the range 20 to 30 ppm and the S/F ratio is in the range 1.2 to 1.4.

Clearly, the fraction which is rich in para-xylene and the fraction which is depleted in para-xylene can be distilled to free them of desorbent. The fraction which is depleted in solvent and free of desorbent, possibly containing a minimal quantity of water, can be isomerised using known isomerisation processes and the isomerate which is rich in para-xylene, possibly free of light compounds, can be recycled at least in part to the adsorption and desorption zone.

The fraction which is rich in para-xylene can be crystallized, normally at high temperature, for example at over −30° C. in accordance with U.S. Pat. No. 5,401,476 and International application WO 96-20 908, hereby incorporated by reference, which describe the steps of crystallization at one or more temperatures.

The solvent which is generally used is toluene or para-diethylbenzene, for example. It can be recycled at least in part to the adsorption and desorption step, in a substantially anhydrous state.

It may be advantageous to introduce methanol, in a proportion which is generally below 500 ppm, into the fraction which is rich in para-xylene and free of desorbent but containing a minimal quantity of water, which is intended for crystallization. The crystallization step thus delivers a mother liquor containing water and methanol which is removed, for example by adsorption, and the mother liquor which is thus free of water and methanol is recycled at least in part to the adsorption and desorption step.

The amounts of water in the hydrocarbon phases are, of course, connected to the amounts of water in the zeolite by an adsorption isotherm which substantially does not depend on the nature of the adsorbed hydrocarbon. As indicated by the prior art, a distinction must be made between the water adsorbed on the zeolite which is measured by a loss on ignition at 400° C. measured in the prior art by a loss on ignition at 500° C. (termed "relative volatile free basis") and between the water which is far more strongly retained which is measured by a loss on ignition at 900° C. or 1000° C. During measurements at 900° C. or 1000° C., the structure of the zeolite is destroyed and the difference in desorbed water between 400° C. and 1000° C. can be considered to represent the water of constitution. The difference between these two terms is of the order of 1.5% to 2% by weight in faujasites.

The water adsorption isotherm is measured as follows: a batch of solid to be tested is allowed to hydrate in the ambient atmosphere. A plurality of columns each 1 metre in length and one centimetre in diameter (78.5 cm$^3$) are filled with this zeolite and the columns are placed in an oven at 250° C. in a stream of very dry nitrogen 9 less than 10 ppm of water). Each column is allowed to dehydrate for different times to obtain different water contents (which are measured by weighing).

Each column is then placed in a closed circuit comprising a reserve of dry hydrocarbon (minimum volume), a positive displacement piston pump for liquid chromatography and the column. The hydrocarbon reserve is provided with a sample outlet to measure the water content in the hydrocarbon once equilibrium has been reached. The total quantity of hydrocarbon is 100 cm$^3$. In this manner, the quantity of water contained in the hydrocarbon is negligible with respect to that remaining retained on the zeolite.

The adsorption isotherms presented in FIGS. 1 and 2 are thus obtained which relate respectively to KBaY and BaX zeolites measured by the loss on ignition at 400° C. representing the quantity of water (%) adsorbed by the zeolites as a function of the concentration (ppm) of water in the hydrocarbon phase at different temperatures.

The influence of water content on separation by adsorption is studied completely independently of the measurement of the isotherm. In this way, the need for cumulative balances at the water inlets and outlets in the separation unit is avoided, where cumulated errors are often very large.

The separation unit is filled with zeolite which has been activated in a rotary furnace at the time of the final phase of manufacture. Depending on the manufacturing batch, the loss on ignition at 400° C. in the zeolite before charging is in the range 2% to 5%. During charging, the adsorbent partly rehydrates to an indeterminate level (always less than 7%).

When anhydrous conditions are required, dry desorbent is passed over the zeolite until only water contents of less than 1 ppm are measured in effluents from the unit. This operation requires a long time (2 to 3 weeks).

In contrast, when a known water content is required, two controlled flows of desorbent are injected, one of anhydrous product, the other of product saturated with water, and a controlled flow of anhydrous feed is injected (the converse can also be carried out). As an example, if the average water content is to be 50 ppm in the streams entering the unit with respective flow rates of 5 $cm^3$/min of feed and 7 $cm^3$/min of desorbent, 5 $cm^3$/min of anhydrous feed is injected, 5.6 $cm^3$/min of anhydrous solvent and 1.4 $cm^3$/min of solvent which is saturated with water at ambient temperature (430 ppm in the case of toluene).

These conditions are maintained until the weighted average of the water contents at the outlets is substantially 50 ppm; as an example, if water contents of 43 ppm in an extract flow of 5.3 $cm^3$/min and 54 ppm in a raffinate flow of 6.65 $cm^3$/min are respectively obtained, the weighted average at the outlets is 49 ppm which is considered to be acceptable bearing in mind the accuracy of the water content measurements.

The water contents of the inlet and outlet streams are measured using the KARL FISCHER method for contents above 15 ppm. When these contents are below 15 ppm, in line measurements delivered by in line analytical probes are relied upon (PANAMETRIC apparatus, series 1). Calibration is carried out between 15 ppm and 200 ppm, and the extrapolation of this calibration curve for contents in the range 1 to 15 ppm is considered to be valid.

The following examples compare the use of a KBaY zeolite-toluene system with and without water, a KBaY-PDEB system with and without water, a BaX-toluene system with and without water and a BaX-PDEB system with and without water.

BRIEF DESCRIPTION OF DRAWINGS

FIGS. 3, 4 and 5 show the solvent ratio for constant performances as a function of the weighted average of the quantities of water (ppm) contained in the outlets (extract and raffinate) at different temperatures;

FIGS. 6, 7 and 8 show an index of performance as a function of the weighted average of the water content at the outlets, expressed in ppm; and FIG. 9 represents an index of performance for various desorbents as a function of the ratio of desorbent to feed (S/F).

All of the figures are referenced in the following examples:

EXAMPLE 1

Figure 1:
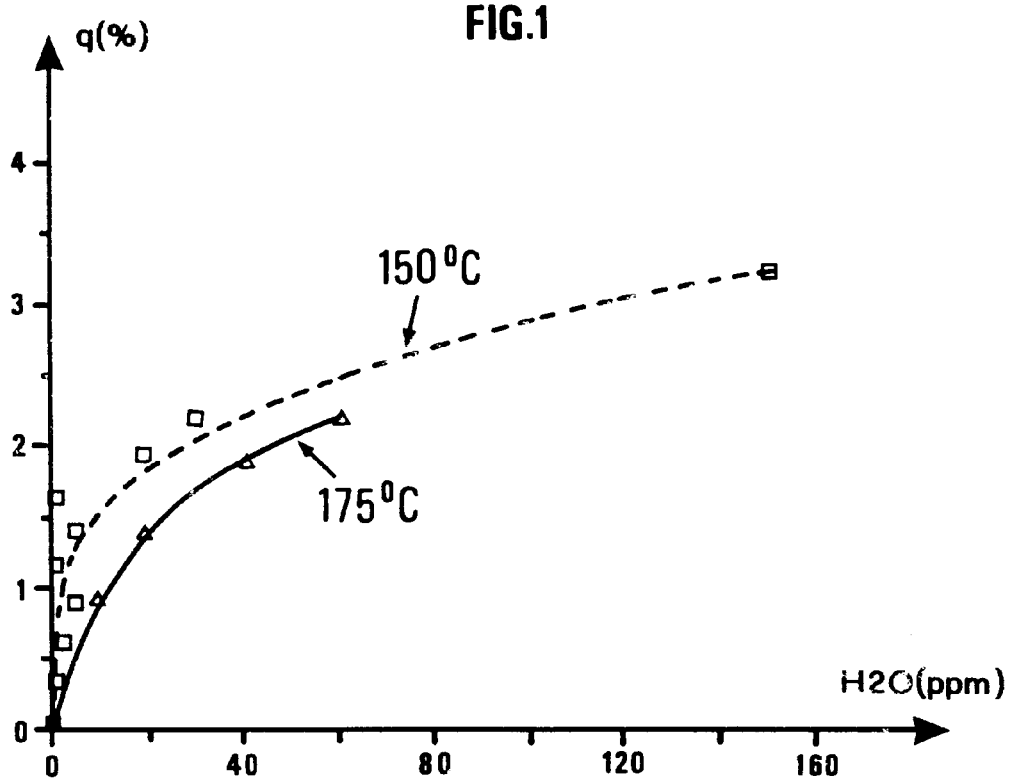
FIGS. 1 and 2 represent the quantity of water adsorbed by various zeolites as a function of concentration (ppm) of water in the hydrocarbon phase, at different temperatures.
Figure 2:
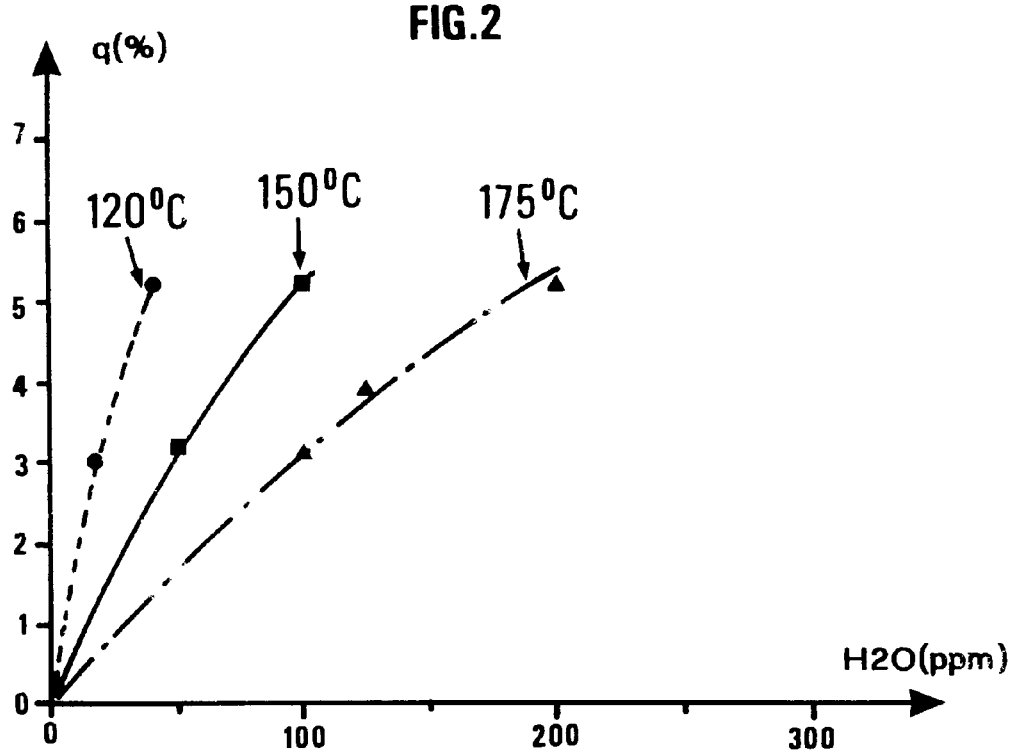

A continuous liquid chromatography pilot unit was produced from 24 columns, 1 m in length and 1 cm in diameter, in series, circulation between the 24$^{th}$ and first column being effected by means of a recycling pump. Either a feed to be separated or a solvent could be injected at each inter-column connection. Either a raffinate or an extract could also be withdrawn. This unit has been described in "Preparative and production scale chromatography processes with applications" edited by G. Barker, G. Ganestos, in the chapter "From batch elution to simulated counter current chromatography" by B. Balannec and G. Hotier (published by Marcel Dekker Inc., New York, 1992). The adsorbent was constituted by Y zeolite exchanged with potassium and barium, the degree of exchange, expressed in normalities, was about 50% for each of the two cations. The zeolite was in the form of spherules 0.315 to 0.5 mm in diameter. The assembly of columns and the distribution valves was placed in an oven at 150° C.

Following the principle of simulated counter-current chromatography, the solvent injection, extract withdrawal, feed injection and raffinate withdrawal were advanced by three columns every six minutes in a direction which was co-current with the circulation of the liquid.

In accordance with the invention, the number of beds to be considered was thus eight. There were six columns (i.e., two beds) between the solvent injection and the extract withdrawal, nine columns (three beds) between the extract withdrawal and the feed injection, three columns (one bed) between the feed injection and the raffinate withdrawal and the last six columns (two beds) were between the raffinate withdrawal and the solvent injection. The performances of the simulated moving bed unit were observed as a function of the weighted average of the water contents in the extract and raffinate, water having been introduced continuously into the columns by means of anhydrous desorbent and saturated desorbent as described above. For the first point on the curve in FIG. 3, the conditions of Example 1 of U.S. Pat. No. 5,401,476 were repeated. 7.2 $cm^3$/min of toluene and 5 $cm^3$/min of feed were continuously injected (ambient conditions). 5.40 $cm^3$/min of extract and 6.74 $cm^3$/min of raffinate were withdrawn, also continuously; the loss was about 5%. During the first period of the cycle, eight in all, solvent was injected into column 1, extract was withdrawn from the outlet from column 6, feed was injected into column 15, and raffinate was withdrawn from the outlet from column 18. During the two first periods of the cycle, the flow rate of the recycling pump was 38.7 $cm^3$/min at ambient temperature; during the third period, the flow rate was 45.5 $cm^3$/min; during the three following periods it was 40.5 $cm^3$/min and during the last two periods the flow rate was 45.9 $cm^3$/min. The average recycle flow rate was thus 42 $cm^3$/min. Para-xylene was obtained with a purity of 92.2% and the recovery rate was 98.1%. The pressure decreased approximately linearly from 30 bar to 5 bar. The following table shows the balance of the unit in the steady state:

| Flow rate | Feed 5 $cm^3$/min | Solvent 7.2 $cm^3$/min | Extract 5.40 $cm^3$/min | Raffinate 6.74 $cm^3$/min |
| --- | --- | --- | --- | --- |
| Toluene | | 99.9% | 79.30% | 43.29% |
| Ethylbenzene | 17% | | 1.07% | 11.72% |
| m-xylene | 4% | | 0.40% | 32.30% |
| o-xylene | 18% | | 0.15% | 12.40% |
| p-xylene | 21% | | 19.08% | 0.29% |

A first mode of operating the unit consisted of reducing the flow rate of desorbent (toluene) while keeping the flow rate of the feed constant. The purity and yield had to be kept approximately constant; this was achieved by adjusting the extract-raffinate balance, the flow rates in zones 2 and 3 and the permutation periods remaining constant, while the flow rates in zones 1 and 4 were adjusted by increasing the flow rate in zone 4 and reducing the flow rate in zone 1.

This mode of operation approached the type of operation in an industrial unit, however it was difficult to obtain points for iso-purity and iso-yield. Variations of the order of 1% were tolerated in the purity and yield provided that the geometric mean of the purity and yield did not vary by more than 0.3%.

FIG. 3 shows that the solvent flow rate was minimised at 150° C. for an average water content of 5 ppm: the solvent to feed ratio was 1.27/1 while that for an anhydrous solvent (as in U.S. Pat. No. 5,401,476) was 1.44/1.

EXAMPLE 2 (FIG. 4)

The experiment was repeated, increasing the operating temperature from 150° C. to 175° C. The purity and yield performances were kept identical to the experiments at 150° C. for solvent ratios which were practically identical for the anhydrous zeolite and for the optimum water content. However, FIG. 4 shows that the optimum water content was not 5 ppm but 10 ppm.

This corresponded to an optimum water content in the zeolite of 0.4% to 0.5% (loss on ignition at 400° C.), which was impossible to measure directly with high enough accuracy.

EXAMPLE 3 (FIG. 5)

The experiment at 175° C. was repeated with 98% pure para-diethylbenzene as the desorbent (the impurities were mainly constituted by meta- and ortho-diethylbenzene). FIG. 5 shows that the solvent ratio could be reduced to about 0.1/1 and the optimum performance was again at 10 ppm of water in the hydrocarbon. This gain in solvent ratio could be linked to the PX-desorbent selectivity which was 0.55 for toluene and 0.72 for para-diethylbenzene.

EXAMPLE 4 (FIG. 6)

The same unit was charged with BaX zeolite in the form of 0.3 mm to 0.8 mm spherules containing 22% of clay based binder. The residual sodium content after exchange was less than 3% of the cations (expressed as the normality).

Only 12 columns were used instead of 24 and the permutations were carried out on all of the columns instead of every three columns as above. There were three beds in each zone. The permutation period was one minute, the ratio between the average recycle rate and the feed was 4.5/1, the solvent ratio was kept constant at 1.25/1, the extract to raffinate ratio was 0.40/1 and the feed flow rate was 8 cm³/min. The productivity was much higher compared with the preceding case due to a reduction in the loss on ignition. The unit was operated at 175° C. and the desorbent was para-diethylbenzene.

A performance index can be defined: IP=( yield)×( purity). The flow rates in the zones were slightly adjusted to retain a reasonable balance between purity and yield (never more than 6% apart). FIG. 6 shows that the performance index for BaX zeolite was a maximum for a water content which was about ten times higher than with KBaY zeolite; on the other hand, the performances of the BaX zeolite were far lower than those for KBaY zeolite when these products were anhydrous while they were substantially higher at the optimum water content. This has never been taught in the prior art.

EXAMPLE 7 (FIG. 7)

The same experiment was repeated at 150° C. Apart from a considerably higher loss on ignition (increase of about 70%), lower performances were noted a long with a different optimum water content in the hydrocarbon (50 to 60 ppm (see FIG. 7)).

EXAMPLE 6 (FIG. 8)

Examples 4 and 5 were repeated except that the solvent was toluene and the temperature was 120° C.: maximum performance was obtained this time for a water content in the hydrocarbon (weighted average of outlets) of about 25 ppm, the extract to raffinate ratio being about 0.7/1 (see FIG. 8).

EXAMPLE 7 (FIG. 9)

Example 4 was repeated, this time fixing the water content at the optimum, i.e., 90 ppm, and the solvent/feed ratio was varied. The feed contained only 4% of ethylbenzene for 22.5% of para-xylene. It also contained 23.5% of ortho-xylene, 1.5% of toluene and 48.5% of meta-xylene. Since this feed was easier to treat, the injected flow rate could be higher, i.e., 10 cm³/min. The ratio of recycle to feed was reduced to 4.4/1 and the permutation period was reduced to 50 seconds. It was seen that above a solvent to feed ratio of 1.45/1, the performances remained identical. By reducing the desorbent flow rate to 8 cm³/min, it was realised that it was possible to again obtain purities of more than 75% for solvent ratios of less than 1, sufficient for purification by crystallization which constitutes the second step of the process (see FIG. 9).

When the desorbent PDEB was replaced by toluene, the performances were slightly poorer and the flow rates were different (the flow rates in zone 1 and zone 4 were higher and the extract to raffinate ratio had to be increased). The importance of using toluene was to be able to treat feeds containing large amounts of $C_9$ aromatics.

Depending on whether toluene or para-diethylbenzene was used, the water contained in the extract had to be removed before sending the low purity para-xylene to the crystallization step.

When the desorbent was toluene, impure para-xylene was withdrawn (substantially free of water) from the bottom of the extract column. Liquid water was withdrawn from the head of the columns for distilling extract and raffinate, by means of the decanting plate, and constituents which were lighter than toluene were purged continuously or periodically. About 3 to 10 plates lower, substantially anhydrous toluene was withdrawn from a withdrawal plate.

When the desorbent was para-diethylbenzene and the feed to be treated contained a little toluene, it was also possible to operate in this manner (water and toluene were withdrawn from the head of the distillation column in this case) and substantially anhydrous impure para-xylene was withdrawn about 10 plates down.

It was also possible not to use this pasteurisation zone, cool the para-xylene, decant the water at about 10° C. then send the water-saturated para-xylene to the crystallization step. In this case, if crystallization was carried out at a temperature of less than 0° C., methanol was generally injected to prevent an accumulation of ice in the crystallization equipment. Before re-injecting the mother liquor from the crystallization step to the adsorption step, the water and methanol had to be removed by adsorption or by distillation.

Regarding the raffinate which had been freed of solvent, it could contain up to 200 ppm of water without any detriment to the isomerisation catalyst.

We claim:

1. In a process for separating para-xylene from a feed comprising a mixture of aromatic $C_8$ isomers containing para-xylene by contacting the feed with a zeolite in a column under simulated moving bed adsorption conditions in the presence of at least one desorbent such that a fraction rich in para-xylene and a fraction depleted in para-xylene are obtained, and further subjecting the fraction rich in para-xylene to at least one crystallizing step to produce substantially pure para-xylene, the improvement comprises introducing a stream of water into the feed, into the desorbent, into a recycling stream for one flux in the column, or into any combination thereof such that the weighted average of the water contents measured in the fraction which is rich in para-xylene and in the fraction which is depleted in para-xylene is in the range of 1 to 250 ppm and that the ratio S/F of the flow rate of the desorbent to that of the feed during the simulated moving bed adsorption is in the range of 0.6 to 2.5.

2. A process according to claim 1, in which the simulated moving bed adsorption step is carried out at a temperature of 140° C. to 160° C. with a Y zeolite exchanged with barium and potassium, the weighted average of the water contents is in the range 3 to 6 ppm and the S/F ratio is in the range 1.15 to 1.35.

3. A process according to claim 1, in which the simulated moving bed adsorption step is carried out at a temperature of 165° C. to 185° C. with a Y zeolite exchanged with barium and potassium, the weighted average of the water contents is in the range 6 to 12 ppm and the S/F ratio is in the range 1.10 to 1.35.

4. A process according to claim 1, in which the simulated moving bed adsorption step is carried out at a temperature of 140° C. to 160° C. with an X zeolite exchanged with barium, the weighted average of the water contents is in the range 45 to 70 ppm and the S/F ratio is in the range 1 to 1.25.

5. A process according to claim 1, in which the simulated moving bed adsorption step is carried out at a temperature of 165° C. to 185° C. with an X zeolite exchanged with barium, the weighted average of the water contents is in the range 60 to 130 ppm, and the ratio is in the range 0.95 to 1.2.

6. A process according to claim 5, wherein the weighted average is 90 to 110 ppm.

7. A process according to claim 1, in which the simulated moving bed adsorption step is carried out at a temperature of 140° C. to 160° C. with a Y or X zeolite exchanged with potassium, the weighted average of the water contents is in the range 5 to 10 ppm and the S/F ratio is in the range 1.2 to 1.4.

8. A process according to claim 1, in which the simulated moving bed adsorption is carried out at a temperature of 165° C. to 185° C. with an X zeolite exchanged with potassium, the weighted average of the water contents is in the range 10 to 20 ppm and the S/F ratio is in the range 1.2 to 1.4.

9. A process according to claim 1, in which the simulated moving bed adsorption is carried out at a temperature of 110° C. to 130° C. with an X zeolite exchanged with barium, the weighted average of the water contents is in the range 20 to 30 ppm and the S/F ratio is in the range 1.2 to 1.4.

10. A process according to claim 1, in which the fraction which is rich in para-xylene and the fraction which is depleted in para-xylene from the simulated moving bed adsorption step are distilled to free them of desorbent, the fraction which is rich in para-xylene and substantially free of desorbent undergoing the crystallization step.

11. A process according to claim 10, in which the desorbent is toluene or para-diethylbenzene and is recycled at least in part to the simulated moving bed adsorption step in a substantially anhydrous state.

12. A process according to claim 11, in which methanol is introduced into the fraction which is rich in para-xylene substantially free of desorbent but containing a quantity of water, before the crystallization step.

13. A process according to claim 10, in which methanol is introduced into the fraction which is rich in para-xylene substantially free of desorbent but containing a quantity of water, before the crystallization step.

14. A process according to claim 13, in which the crystallization step delivers a mother liquor containing water and methanol and in which the water and methanol are removed from the mother liquor before recycling it at least in part to the simulated moving bed adsorption step.

15. A process according to claim 10, in which the fraction which is depleted in para-xylene and free of desorbent is isomerised.

16. A process according to claim 1, wherein said weighted average is in the range of 3 to 120 ppm.

17. A process according to claim 1, wherein said ratio S/F is 0.8 to 1.5.

18. A process according to claim 1, wherein said ratio S/F is 1 to 1.35.

19. In a process for separating para-xylene from a feed comprising a mixture of aromatic $C_8$ isomers containing para-xylene by contacting the feed with a zeolite in a column under simulated moving bed adsorption conditions in the presence of at least one desorbent such that a fraction rich in para-xylene and a fraction depleted in para-xylene are obtained, the improvement comprises introducing a stream of water into the feed, into the desorbent, into a recycling stream for one flux in the column, or into any combination thereof such that the weighted average of the water contents measured in the fraction which is rich in para-xylene and in the fraction which is depleted in para-xylene is in the range of 1 to 250 ppm and that the ratio S/F of the flow rate of the desorbent to that of the feed during the simulated moving bed adsorption is in the range of 0.6 to 2.5.

20. A process according to claim 19, in which the simulated moving bed adsorption step is carried out at a temperature of 140° C. to 160° C. with a Y zeolite exchanged with barium and potassium, the weighted average of the water contents is in the range 3 to 6 ppm and the S/F is in the range 1.15 to 1.35.

21. A process according to claim 19, in which the simulated adsorption step is carried out at a temperature of 165° C. to 185° C. with a Y zeolite exchanged with barium and potassium, the weighted average of the water contents is in the range 6 to 12 ppm and the S/F ratio is in the range 1.10 to 1.35.

22. A process according to claim 19, in which the simulated moving bed adsorption step is carried out at a temperature of 140° C. to 160° C. with an X zeolite exchanged with barium, the weighted average of the water contents is in the range 45 to 70 ppm and the S/F ratio is in the range 1 to 1.25.

23. A process according to claim 17, in which the simulated moving bed adsorption step is carried out at a temperature of 165° C. to 185° C. with an X zeolite exchanged with barium, the weighted average of the water contents is in the range 60 to 130 ppm, and the S/F ratio is in the range 0.95 to 1.2.

24. A process according to claim 19, in which the simulated moving bed adsorption step is carried out at a temperature of 140° C. to 160° C. with a Y or X zeolite exchanged with potassium, the weighted average of the water contents is in the range 5 to 10 ppm and the S/F ratio is in the range 1.2 to 1.4.

25. A process according to claim 19, in which the simulated moving bed adsorption is carried out at a temperature of 165° C. to 185° C. with an X zeolite exchanged with potassium, the weighted average of the water contents is in the range 10 to 20 ppm and the S/F ratio is in the range 1.2 to 1.4.

26. A process according to claim 19, in which the simulated moving bed adsorption is carried out at a temperature of 110° C. to 130° C. with an X zeolite exchanged with barium, the weighted average of the water contents is in the range 20 to 30 ppm and the S/F ratio is in the range 1.2 to 1.4.

* * * * *